United States Patent
Turek et al.

(10) Patent No.: US 7,346,203 B2
(45) Date of Patent: Mar. 18, 2008

(54) METHODS AND APPARATUS FOR PROCESSING IMAGE DATA TO AID IN DETECTING DISEASE

(75) Inventors: Matthew William Turek, Ballston Lake, NY (US); Joseph Leagrand Mundy, Barrington, RI (US); Tony Chi-shao Pan, Hilliard, OH (US); Peter Henry Tu, Schenectady, NY (US); James Vradenburg Miller, Clifton Park, NY (US); Robert August Kaucic, Jr., Niskayuna, NY (US); Xiaoye Wu, Rexford, NY (US); Paulo Ricardo dos Santos Mendonca, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 750 days.

(21) Appl. No.: 10/717,861

(22) Filed: Nov. 19, 2003

(65) Prior Publication Data

US 2005/0105788 A1    May 19, 2005

(51) Int. Cl.
  *G06K 9/00* (2006.01)
  *G06K 9/34* (2006.01)
  *A61B 5/00* (2006.01)
  *A61B 5/05* (2006.01)
(52) U.S. Cl. ............... 382/131; 382/173; 600/300; 600/407; 600/410
(58) Field of Classification Search ........ 382/128–131, 382/294; 600/407, 403; 705/2, 3; 128/922, 128/923
See application file for complete search history.

(56) References Cited

U.S. PATENT DOCUMENTS

| | | | | |
|---|---|---|---|---|
| 5,235,510 | A * | 8/1993 | Yamada et al. | 600/300 |
| 6,083,162 | A * | 7/2000 | Vining | 600/407 |
| 6,234,964 | B1 * | 5/2001 | Iliff | 600/300 |
| 6,289,115 | B1 * | 9/2001 | Takeo | 382/130 |
| 6,336,082 | B1 | 1/2002 | Nguyen et al. | |
| 6,356,780 | B1 * | 3/2002 | Licato et al. | 600/407 |
| 6,418,334 | B1 * | 7/2002 | Unger et al. | 600/407 |
| 6,819,785 | B1 * | 11/2004 | Vining et al. | 382/128 |
| 6,901,277 | B2 * | 5/2005 | Kaufman et al. | 600/407 |
| 7,158,692 | B2 * | 1/2007 | Chalana et al. | 382/294 |
| 2002/0102012 | A1 * | 8/2002 | Keller et al. | 382/128 |
| 2003/0055331 | A1 * | 3/2003 | Kotmel et al. | 600/410 |
| 2003/0095692 | A1 | 5/2003 | Mundy et al. | |
| 2005/0207630 | A1 * | 9/2005 | Chan et al. | 382/131 |

* cited by examiner

*Primary Examiner*—Andrew W. Johns
*Assistant Examiner*—Andrae Allison
(74) *Attorney, Agent, or Firm*—Fletcher Yoder (57) ABSTRACT

A method for detecting, quantifying, staging, reporting, and/or tracking of a disease includes providing analysis software configured to detect, quantify, stage, report, and/or track a disease utilizing images of a patient. The analysis software is executable on a personal computer of a patient. Patients are then imaged utilizing a medical imaging apparatus and medical images of the patient produced by the imaging apparatus are downloaded to the personal computer of the patient. The imaging and downloading are repeated a plurality of times at intervals selected to provide the analysis software with sufficient images to detect, quantify, stage, report, and/or track the disease in the patient.

75 Claims, 4 Drawing Sheets

METHODS AND APPARATUS FOR PROCESSING IMAGE DATA TO AID IN DETECTING DISEASE

BACKGROUND OF THE INVENTION

This invention relates to methods and apparatus for processing medical image data to aid in the detection and diagnosis of disease, and more particularly, to methods and apparatus for detecting, quantifying, staging, reporting, and/or tracking of diseases such as chronic obstructive pulmonary disease.

Chronic Obstructive Pulmonary Disease (COPD) is a leading cause of death in the United States and other countries. COPD has two main disease processes, namely, tissue destruction (emphysema) and airway inflammation (chronic bronchitis). At present, there is no known treatment that can reverse the progress of the disease. At best, the progress of the disease can only be halted. Thus, there is a premium placed on early disease diagnosis and treatment. With early diagnosis and effective treatment, a patient's quality of life can be improved.

An x-ray chest radiograph system is the more commonly used diagnostic tool useful for the purpose of detecting lung disease in humans. Lung disease such as bronchitis, emphysema and lung cancer are also detectable in chest radiographs and CT. However, CT systems generally provide over 80 separate images for a single CT scan thereby providing a considerable amount of information to a radiologist for use in interpreting the images and detecting suspect regions that may indicate disease.

Suspect regions are defined as those regions a trained radiologist would recommend following through subsequent diagnostic imaging, biopsy, functional lung testing, or other methods. The considerable volume of data presented by a single CT scan presents a time-consuming process for radiologists. Conventional lung cancer screening generally involves a manual interpretation of the 80 or more images by the radiologist. Fatigue is therefore a significant factor affecting sensitivity and specificity of the human reading. In other diseases, such as emphysema, it is difficult for a radiologist to classify the extent of disease progression by only looking at the CT images.

COPD is identified based on symptoms including coughing, wheezing, and shortness of breath (dyspnea). COPD includes a number of respiratory diseases, the most prominent of which are emphysema and chronic bronchitis. COPD affects large airways, small airways and parenchyma in patients. Diseases are typically caused by smoking and air pollution, and are linked to genetic predisposition causing alpha-anti-elastase deficiency.

Emphysema, or airspace destruction, is the most prominent feature of parenchymal change in COPD patients. Emphysema is the result of the loss of elastic recoil of lung tissue. There are four types of emphysema: centrilobular, panlobular or panacinar, distal acinar or paraseptal, and irregular. The first two types contribute to the majority of emphysematous COPD. The classification is based on the anatomical distribution of airspace destruction within a lobule, which is a cluster of acini. Currently, emphysema can be classified only through post mortem examination. Emphysema is typically diagnosed by gross physiological responses, medical imaging and post mortem anatomical inspection. The use of high resolution CT image data is a promising technique for measuring the lung volume for diagnosis purposes. However, one of the more prominent disease indicators is degradation of the alveoli and other tissue changes of the lung which are currently difficult to measure from CT image data.

Detecting emphysema at early stages is most desirable. The damage caused by emphysema is often detected at later stages of the disease and the effects are permanent. Although the effects of emphysema cannot be reversed, early diagnosis of emphysema may enable measures to be taken by the patient to prevent further progression of the damage caused by the disease. Further, as more and more therapy and drug treatments are discovered, it will be desirable to monitor a patient's response to such treatment.

Chronic bronchitis causes anatomical airway narrowing, which reduces lung function. Airway modification typically begins with irritation from smoking and/or air pollution and can be caused/exacerbated by biological infection. Chronic bronchitis is clinically defined by persistent cough and sputum production for more than 3 months in a 2-year period. Chronic bronchitis can be classified into simple chronic bronchitis, obstructive bronchitis and chronic asthmatic bronchitis. In simple chronic bronchitis, no sputum is produced. Chronic asthmatic bronchitis involves hyperreactivity of the airways. In obstructive chronic bronchitis, airflow is hindered by airway modification. Chronic bronchitis is currently staged using Reid index post mortem. High resolution CT may enable scoring chronic bronchitis using Reid index in vivo.

Bronchial wall cross-sectional area is a key indicator in the diagnosis and staging of COPD. Measuring airway cross-sectional area from medical images (for instance CT) will enable physicians to track disease progression and accelerate clinical trials. Bronchial passages appear in CT images as small dark regions surrounded by bright regions. The dark area is the lumen while the bright area is composed of both the bronchial wall and any attaching or adjacent blood vessels. In measuring the airway wall cross-sectional area, one must not incorporate the thickness of the attaching or adjacent blood vessels.

If the airway is isolated, with no attaching or adjacent blood vessels, the airway can be measured using a variety of standard image processing and computer vision techniques. When the imaged airway has attached of adjacent blood vessels, an example of traditional approach has been to manually select a ray from the center of the lumen that passes through the airway wall at a point where the are no blood vessels. The measure of the wall thickness along this single ray is used to estimate the airway cross-sectional area.

Some known diagnosis techniques have attempted to use simple Computed Tomographic (CT) images to attempt to quantify emphysema. However, known techniques are not based on an underlying model of the disease, and the reliability of the results obtained with these techniques can be affected by variable scan parameters and scanner calibration as well as other disease pathologies. In addition, known techniques do not provide estimates of the rate or location of tissue destruction.

BRIEF DESCRIPTION OF THE INVENTION

The present invention therefore provides, in some configurations, a method for at least one of detecting, quantifying, staging, reporting, or tracking of a disease. The method includes providing analysis software configured to detect, quantify, stage, report, and/or track a disease utilizing images of a patient. The analysis software is executable on a personal computer of a patient. Patients are then imaged utilizing a medical imaging apparatus and medical images of the patient produced by the imaging apparatus are downloaded to the personal computer of the patient. The imaging and downloading are repeated a plurality of times at intervals selected to provide the analysis software with sufficient images to detect, quantify, stage, report, and/or track the disease in the patient.

Some configurations of the present invention provide a network for detecting, quantifying, staging, reporting, and/or tracking of a disease. The network includes analysis software executable on personal computers of patients. This software includes instructions configured to instruct the personal computer to detect, quantify, stage, report, and/or track a disease utilizing images of a patient. At least one imaging apparatus is also included in the network. The imaging apparatus is configured to produce medical images of patients. Also provided is an interface for transferring scanned images of a patient to a personal computer of the imaged patient.

Some configurations of the present invention provide a portable computing device that is configured to download medical images of a patient produced by an imaging apparatus to the portable computing device. The portable computing device is also configured to analyze the downloaded medical images to detect, quantify, stage, report, and/or track a disease in the patient and report analysis results to the patient; and to transmit results of the analysis to a remote database.

Still other configurations of the present invention provide a method for performing a drug treatment trial. This method includes providing analysis software configured to detect, quantify, stage, report, and/or track a disease utilizing images of a patient. This analysis software is executable on personal computers of a plurality of patients. The method further includes imaging the patients with medical imaging apparatus to produce medical images of the patients, downloading the medical images of each imaged patient to the personal computer of the imaged patient. The imaging and downloading are repeated a plurality of times at intervals selected to provide the analysis software with sufficient images to detect, quantify, stage, report, and/or track the disease in each patient. The method further includes analyzing the medical images utilizing the personal computers of each patient to detect, quantify, stage, report, and/or track a disease in the patient and uploading results of the analysis from each patient's personal computer to a database for further analysis and evaluation.

Still other configurations of the present invention provide a method and apparatus for tracking a changeable parameter of one or both of a person or object in a population of such persons or objects. The method includes providing analysis software configured to track at least one changeable parameter utilizing images of the person or object. The analysis software is executable on a personal computer in the possession of the person or in the possession of a person possessing the object. Also included in the method is imaging the person or the object with an imaging apparatus and downloading images of the person or object produced by the imaging apparatus to the personal computer. The imaging and downloading are repeated a plurality of times at intervals selected to provide the analysis software with sufficient images to track the changeable parameter.

Still other configurations of the present invention provide a method for at least one of detecting, quantifying, staging, reporting, or tracking of a disease. The method includes providing analysis software configured to at least one of detect, quantify, stage, report, or track a disease utilizing images of a patient, imaging the patient with a medical imaging apparatus, downloading medical images of the patient produced by the imaging apparatus to a computer, and repeating the imaging and downloading a plurality of times. The repetition is performed at intervals selected to provide the analysis software with sufficient images to detect, quantify, stage, report, and/or track the disease in the patient.

Still other configurations of the present invention provide a network for at least one of detecting, quantifying, staging, reporting, or tracking of a disease. The network includes analysis software executable on a computer, wherein the software includes instructions configured to instruct the computer to detect, quantify, stage, report, and/or track a disease utilizing images of a patient. The network also includes at least one imaging apparatus configured to produce medical images of patients, and an interface for transferring scanned images of a patient to the computer.

Yet other configurations of the present invention provide a method for performing a drug treatment trial. The method includes providing analysis software configured to at least one of detect, quantify, stage, report, or track a disease utilizing images of a patient. The analysis software is executable a computer. The method further includes imaging the patients with medical imaging apparatus to produce medical images of the patients, downloading the medical images of each imaged patient to the computer, and repeating said imaging and downloading a plurality of times. The repetition is performed at intervals selected to provide the analysis software with sufficient images to detect, quantify, stage, report, and/or track the disease in each patient. The method further includes analyzing the medical images utilizing the computer to detect, quantify, stage, report, and/or track a disease in the patient, and uploading results of the analysis from the computer to a database for further analysis and evaluation.

It will be seen that various configurations of the present invention allow the diagnosis, stating and/or prediction of COPD from medical images such as computed tomography scans. The automated features provided by the invention via personal computers and software can run with or without the supervision of an experienced physician or scientist, and allow effective disease diagnosis and treatment that can improve a patient's quality of life. Other configurations economically provide tracking of changeable parameters of either a person or an object utilizing imaging devices at a centralized location and personal computers, such as portable computers, of individuals.

DETAILED DESCRIPTION OF THE INVENTION

Example configurations of systems and processes that facilitate detecting, quantifying, staging, reporting and/or tracking of diseases are described below in detail. It will be appreciated that, with appropriate modification, other changeable parameters relating to persons or objects may also be tracked utilizing configurations of the present invention. A technical effect of the systems and processes described herein include at least one of facilitating automatic tracking of changeable parameters relating to a disease of a patient or other measurable parameters, and/or automated extraction of information relating to these parameters from a plurality of individuals or other tracked objects.

Figure 1:
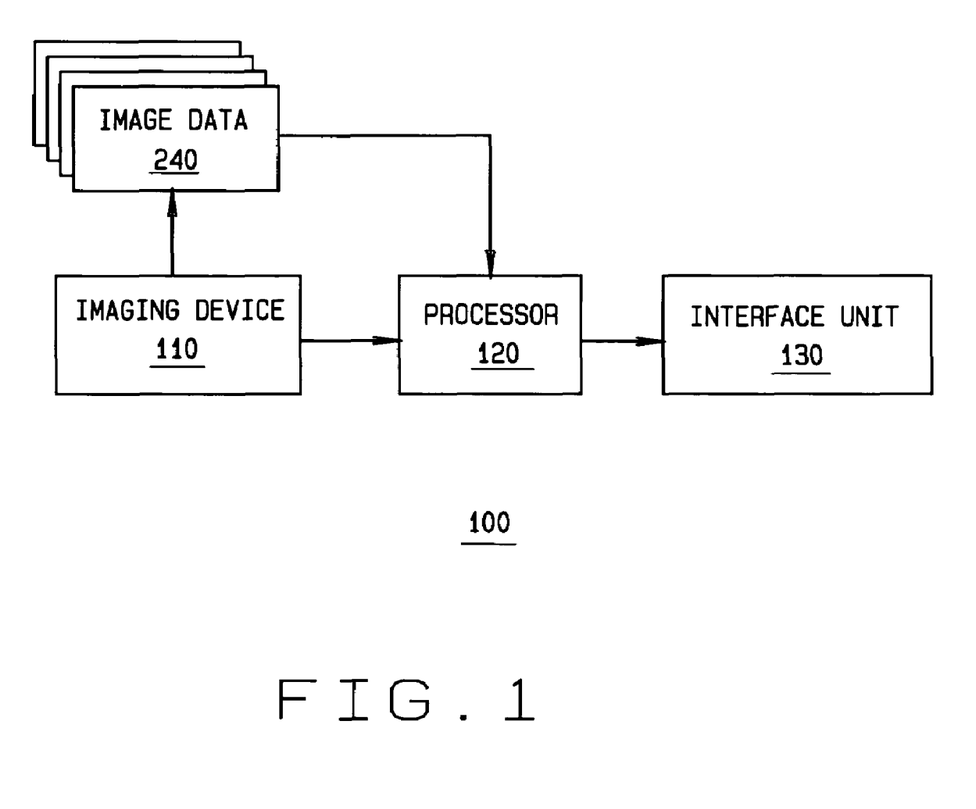
FIG. 1 is a general block diagram of a system 100 for disease detection.

Referring to FIG. 1, a general block diagram of a system 100 for disease detection is shown. A technical effect of the system described in FIG. 1 is achieved by a user collecting and transmitting images of a patient or other object. System 100 includes an imaging device 110, which can be selected from a number of medical imaging devices known in the art for generating a plurality of images. Most commonly, computed tomography (CT) and magnetic resonance imaging (MRI) systems are used to generate a plurality of medical images.

During a CT imaging session, a patient is placed within the imaging device and is exposed to a plurality of x-rays measured with a series of x-ray detectors. A beam of x-rays passes through a particular thin cross-section or "slice" of the patient. The detectors measure the amount of transmitted radiation. This information is used to compute the x-ray attenuation coefficient for sample points in the body. A gray scale image is then constructed based upon the calculated x-ray attenuation coefficients. The shades of gray in the image represent the amount of x-ray absorption of every point within the slice. The slices obtained during a CT session can be reconstructed to provide an anatomically correct representation of the area of interest within the body that has been exposed to the x-rays.

During a MR imaging session, the patient is placed inside a strong magnetic field generated by a large magnet. Magnetized protons within the patient, such as hydrogen atoms, align with the magnetic field produced by the magnet. A particular slice of the patient is exposed to radio waves that create an oscillating magnetic field perpendicular to the main magnetic field. The slices can be taken in any plane chosen by the physician or technician (hereinafter the "operator") performing the imaging session. The protons in the patient's body first absorb the radio waves and then emit the waves by moving out of alignment with the field. As the protons return to their original state (before excitation), diagnostic images based upon the waves emitted by the patient's body are created. Like CT image slices, MR image slices can be reconstructed to provide an overall picture of the body area of interest. Parts of the body that produce a high signal are displayed as white in an MR image, while those with the lowest signals are displayed as black. Other body parts that have varying signal intensities between high and low are displayed as some shade of gray.

Once initial MR or CT images (or any other type of images) have been obtained, the images are generally segmented. The segmentation process classifies the pixels or voxels of an image into a certain number of classes that are homogeneous with respect to some characteristic (i.e. intensity, texture, etc.). For example, in a segmented image of the brain, the material of the brain can be categorized into three classes: gray matter, white matter, and cerebrospinal fluid. Individual colors can be used to mark regions of each class after the segmentation has been completed. Once the segmented image is developed, surgeons can use the segmented images to plan surgical techniques.

Generally, creating a segmented CT or MR image involves several steps. A data set is created by capturing CT or MR slices of data. Through the segmentation process, a gray scale value is then assigned to each point in the data set. In some configurations, each type of material in the data is assigned a specific value and, therefore, each occurrence of that material has the same gray scale value. For example, all occurrences of bone in a particular image may appear in a particular shade of light gray. This standard of coloring allows the individual viewing the image to easily understand the objects being represented in the images.

In some configurations and referring to FIG. 1, a medical imaging system 100 includes an imaging device 110, a processor 120 and an interface unit 130. Imaging device 110 is adapted to generate a plurality of image data sets 240 and is, for example and without limitation, a computed tomography (CT), a magnetic resonance (MR) scanner, or an x-ray imaging apparatus, which may include a multiple view x-ray imaging apparatus. In CT and MR contexts, image data is acquired during a "scan." In some configurations, images are acquired using a CT imaging device. Processor 120 is configured in an manner described in greater detail below with reference to FIG. 2. Processor 120 is also configured to perform computation and control functions for well-known image processing techniques such as reconstruction, image data memory storage, segmentation, etc. Processor 120 in some configurations comprises a central processing unit (CPU), which may be a single integrated circuit such as a microprocessor, or which may comprise any suitable number of integrated circuit devices and/or circuit boards providing the functions of a central processing unit. Processor 120 may further include memory of any type known to those skilled in the art. Such memory (not shown separately in FIG. 1) may include Dynamic Random Access Memory (DRAM), Static RAM (SRAM), flash memory, cache memory, etc, and may be a single type of memory component or a combination of different types of memory components. Processor 120 is capable of executing stored programs in its memory and is responsive to activities that may occur in the course of image acquisition and image viewing.

As used herein, "adapted to," "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to perform a sequel to provide an output in response to given input signals.

Interface unit 130 is coupled to processor 120 and is configured to provide communication between human users and system 100. Processor 120 is further configured to perform computations and transmit results to interface unit 130 in such a manner that a human user is capable of interpreting the transmitted information. Transmitted information may include images in 2D or 3D, color and gray scale images, and text messages regarding diagnosis and detection information. Interface unit 130 may be a personal computer, an image workstation, a hand held image display unit or any conventional image display platform generally grouped as part of a CT or MRI system.

All data gathered from multiple scans of the patient is regarded as one data set. Each data set comprises smaller units, either pixels or voxels. In the case of two-dimensional data sets, images comprise pixel units. "Pixels," as used herein, are points in two-dimensional space that can be referenced using two dimensional coordinates, usually x and y. Each pixel in an image is surrounded by eight other pixels, the nine pixels forming a three-by-three square. (Those of ordinary skill in the art will understand that pixels at the edge and corner boundaries of an image are not surrounded on all sides by other pixels, and thus cannot be central pixels of a three-by-three square.) These eight other pixels, which surround the center pixel, are considered the eight-connected neighbors of the center pixel. When the data set is three-dimensional, the image is displayed in units called voxels. A voxel is a point in three-dimensional space that can be referenced using three-dimensional coordinates, usually x, y and z. Each voxel is surrounded by twenty-six other voxels. (As is the case with pixels, voxels at the edge ad corner boundaries of the three-dimensional space are not surrounded on all sides by other voxels, and thus cannot be central voxels of a three-by-three-by-three cube.) These twenty-six voxels can be considered the twenty-six connected neighbors of the original voxel.

An appropriate patient scanning protocol is used to acquire image data. For example, chest exams using CT or MRI typically require a patient (subject) to hold his or her breath to reduce motion artifacts in the image data resulting from patient respiration. Usually, CT or MRI exams are taken during full inspiration or full expiration. Further, contrast agents may be used to attenuate x-ray radiation in particular body areas. Contrast agents improve differentiation between tissues affected by the contrast agents and tissues that are not affected. In a CT image, a CT number difference between contrasted and non-contrasted tissues is increased. Contrast agents are administered to the patient orally, intravenously or rectally.

Once image data is acquired from the imaging methods described above, image processor 120 is adapted to perform processing to measure disease relevant tissue changes (for example, bronchial wall cross-sectional areas). Bronchial wall cross-sectional area is used in the diagnosis and staging of chronic bronchitis, whereas tissue changes and lung volume are used in the diagnosis and staging of emphysema, both of which relate to chronic obstructive pulmonary disease (COPD).

Measuring cross-sectional area of bronchial walls, also referred to as "airways," from medical images (e.g. CT image data) enables physicians to track disease progression and accelerate clinical trials. Bronchial passages typically appear in CT images as small dark regions surrounded by bright regions. The dark area is the lumen while the bright area is composed of both the bronchial wall and any attaching or adjacent blood vessels. In measuring the airway wall cross-sectional area, it is necessary to isolate the airways from the attaching or adjacent blood vessels so that the thickness measurement does not incorporate such vessels.

In some configurations of the present invention, a method for measuring a tubular structure is provided. As used herein, a "tubular structure" refers to a hollow anatomical structure having an inner wall and an outer wall and a circular or elliptical shape. Examples of tubular structures include bronchial walls and airways. Other anatomical structures such as arteries and other major or significant blood vessels may also benefit from various configurations of measurement techniques described herein, as may other non-anatomical tubular structures in industrial or non-destructive testing environments. For example, one configuration of a method for measuring tubular anatomical structures from acquired image data comprises utilizing at least one segmentation process to isolate a selected tubular anatomical structure of interest and measuring at least one attribute of the selected structure.

Figure 2:
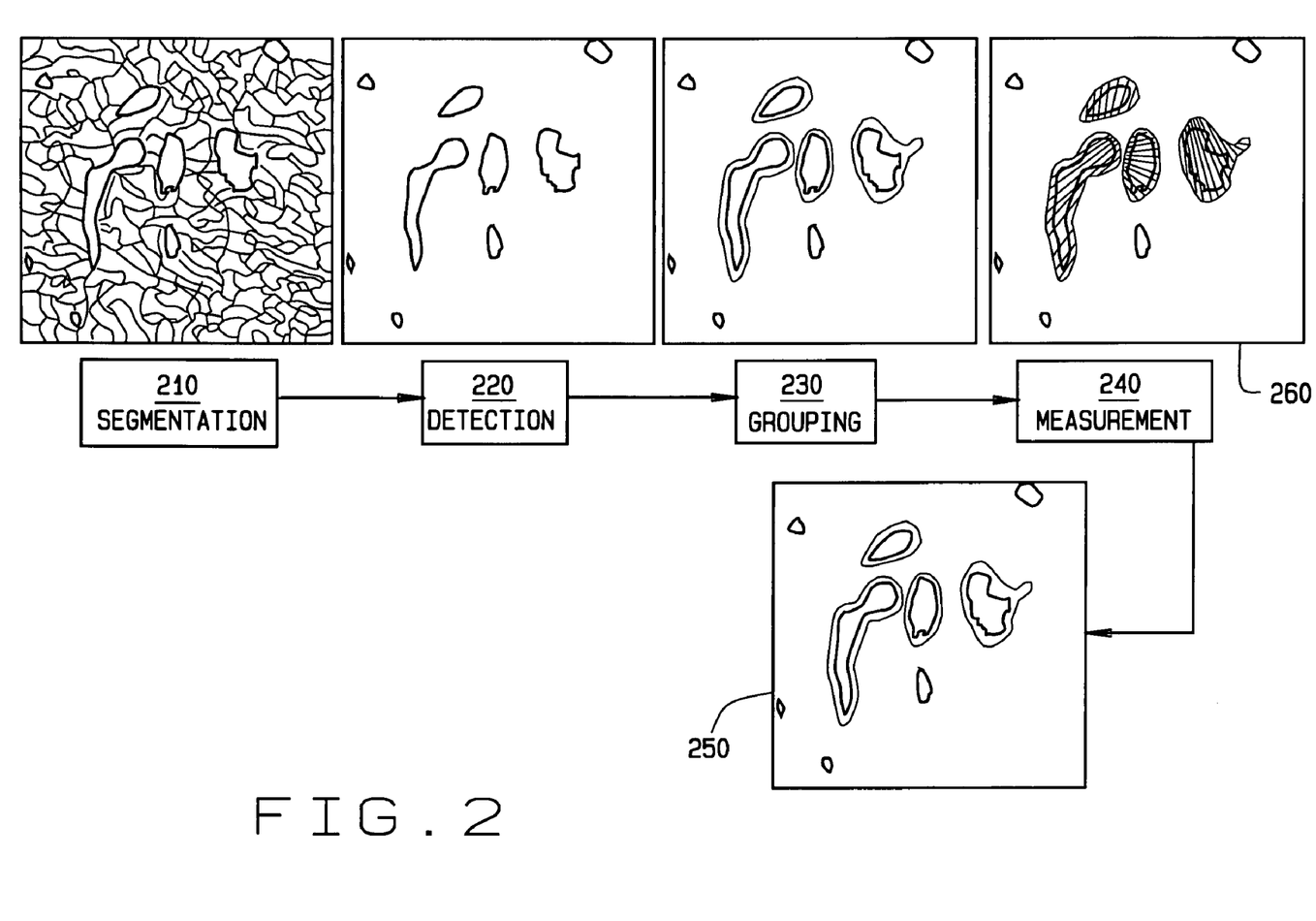
FIG. 2 is a flow chart representative of the analysis of tubular anatomical structures.

In various configurations of the present invention and referring to FIG. 2, a tubular anatomical structure is measured. A technical effect of the configuration represented in FIG. 2 is achieved by a user initiating a computer automated procedure that results in the measurement of tubular structures, which may include the automated identification and measurement of lumens in a lung. Measuring an anatomical structure in configurations represented by FIG. 2 comprises utilizing an imaging device to acquire CT or MRI image data of the structure. The acquired image data is segmented into homogeneous regions and airway lumens are detected by a method comprising segmentation 210 (which may be accomplished by any known technique), detecting similar structures 220 (using, for example, intensity values) and grouping like structures 230. Measuring 240 comprises identifying a center of the lumen 250. The center of the lumen can be identified without bias being introduced by the presence of blood vessels.

In embodiments such as those represented by FIG. 2, identifying a center of the lumen 250 comprises fitting an inner ellipse to an inner boundary of the lumen and fitting an outer ellipse to an outer boundary of the lumen at several points along an airway. Ellipse measurements at 240 are used to measure attributes of the tubular structure. Two concentric ellipses constrained to have a center that matches the center of the lumen are fitted. The inner ellipse is fit using an M-estimator because the lumen boundary has few outliers along its boundary. The outer ellipse is fit using a combination of Muse, a known robust estimation technique, and a series of M-estimators. Muse is used to fit a circle to the exterior boundary of the airway to provide a robust estimate of the minor axis of the outer airway boundary and a robust estimate of the noise in the positions of the outer boundary. Along with these robust estimates, Muse labels each of the points along the outer boundary as inliers to the outer airway boundary or outliers to airway boundary (for example, blood vessels). The inliers to the Muse circle are then fit to an ellipse using an M-estimator. The M-estimator is seeded with the Muse circle and Muse estimate of the scale (noise). In some configurations, the M-estimator is used determine the parameters of the ellipse but is not used to calculate a new estimate of the scale (noise). When the M-estimator converges, a new set of inliers to the ellipse is determined from the original set of boundary points (not just the inliers to the Muse circle) using the Muse scale as a distance criterion. The new set of inliers is provided to an M-estimator, which is seeded with the previous ellipse parameters and the Muse scale estimate. In some configurations, the second M-estimator re-estimates the ellipse but does not re-estimate the scale. This process is repeated until the inlier set and the ellipse fit converges. By employing processing as described above, a robust method is provided in which adjacent blood vessels are not incorporated in airway measurements. By treating the lumen center point as invariant, the ellipse fitting problem is advantageously reduced from six parameters to four parameters. Thus, in some of the configurations described herein, the lumen center is taken as an origin so that positional parameters of the ellipse do not need to be estimated.

A lumen detection stage identifies dark regions that are completely surrounded by bright regions. A center of the bright region is determined and rays 260 are cast from the center of the lumen. The rays are distributed so as to intersect a lumen boundary (inner wall) at a fixed interval or arc length. For each ray, an intersection with the lumen boundary (inner wall) and an intersection with the airway (outer wall) are recorded. The latter intersection points may be on the airway wall or on adjacent vessels. These two sets of intersection points are then used to fit ellipses. The data is scaled to fit within a unit square (−1, 1) to improve numerical stability. Muse is used to robustly estimate the minor axis of an ellipse for the outer airway boundary (radius of the Muse circle) and robustly estimate the noise in the positions of the outer airway boundary. Muse also identifies an initial set of inliers, i.e., points belonging to the airway as opposed to points belong to blood vessels. Seeding an M-estimator with these inliers, Muse circle, and Muse scale (and not having the M-estimator estimate the scale) keeps the M-estimator from degrading to a least squares fit to the entire boundary (airway and blood vessels). Using Muse to estimate only a circle reduces the number of parameters to estimate, greatly accelerating the estimation process. Iterative "corralling" of an M-estimator in this fashion allows the estimate to remain robust and fast. The estimation process described above is performed iteratively.

With inner and outer boundaries determined, wall thickness is determined in some configurations as the difference of the area between the airway boundary ellipse and the lumen boundary ellipse. This difference is determined with subpixel accuracy in some configurations. The wall thickness measurement can thereafter be used to calculate average wall thickness, wall thickness variations, volume measurements, two-dimensional (2D) area measurements and volume area distribution. These measurements can be used to diagnose and track the progression of various diseases and stages of COPD. The isolating and measuring steps are repeated for the image data corresponding to the length of the structure of interest to generate the measurements described above for the full length of the structure.

When the processing described above is complete, some configurations of the present invention generate output of the level and progression of the disease. For example, the output may be used for staging a disease in a patient, measuring response to therapy, phenotyping for patient selection to participate in drug trials, measuring stability of an anatomical structure and prediction of rate of change of the disease. As used herein, phenotyping refers to observing physical or biochemical characteristics, as determined by both genetic makeup and environmental influences and to express a specific trait, such as stature or blood type, based on the influences. A phenotype is an individual or group of organisms exhibiting a particular phenotype.

In some configurations, an apparatus for measuring lung airways using acquired image data is provided. The apparatus comprises an imaging device configured to acquire image data and an image processing device responsive to the imaging device for processing images. Referring again to FIG. 1, image processing device 120 is configured to isolate an airway of interest utilizing at least one segmentation process. Image processing device 120 is further configured to fit an inner ellipse to an inner boundary of the airway and an outer ellipse to an outer boundary of the structure of the airway using statistical techniques at a point in the airway, and further configured to generate measurements of the airway using the inner and outer ellipses. The measurements comprise at least one of average wall thickness, wall thickness variations, volume measurements, two-dimensional (2D) area measurements and/or volume area distribution. These one or more measurements are used for at least one of disease diagnosis and/or tracking of disease progression, wherein the disease is chronic obstructive pulmonary disease or asthma. In some configurations, the apparatus includes a display device (interface unit 130) coupled to image processing device 120 and configured to report measurements to a user of the apparatus.

Configurations of the present invention described in previous paragraphs locate suspicious regions in CT lung scans. However, the measuring techniques disclosed herein are also useful for other imaging modalities, such as MRI, X-ray, ultrasound, and positron emission tomography (PET), where measurement of substantially tubular anatomical structures can be used to track or diagnosis a particular disease.

Figure 3:
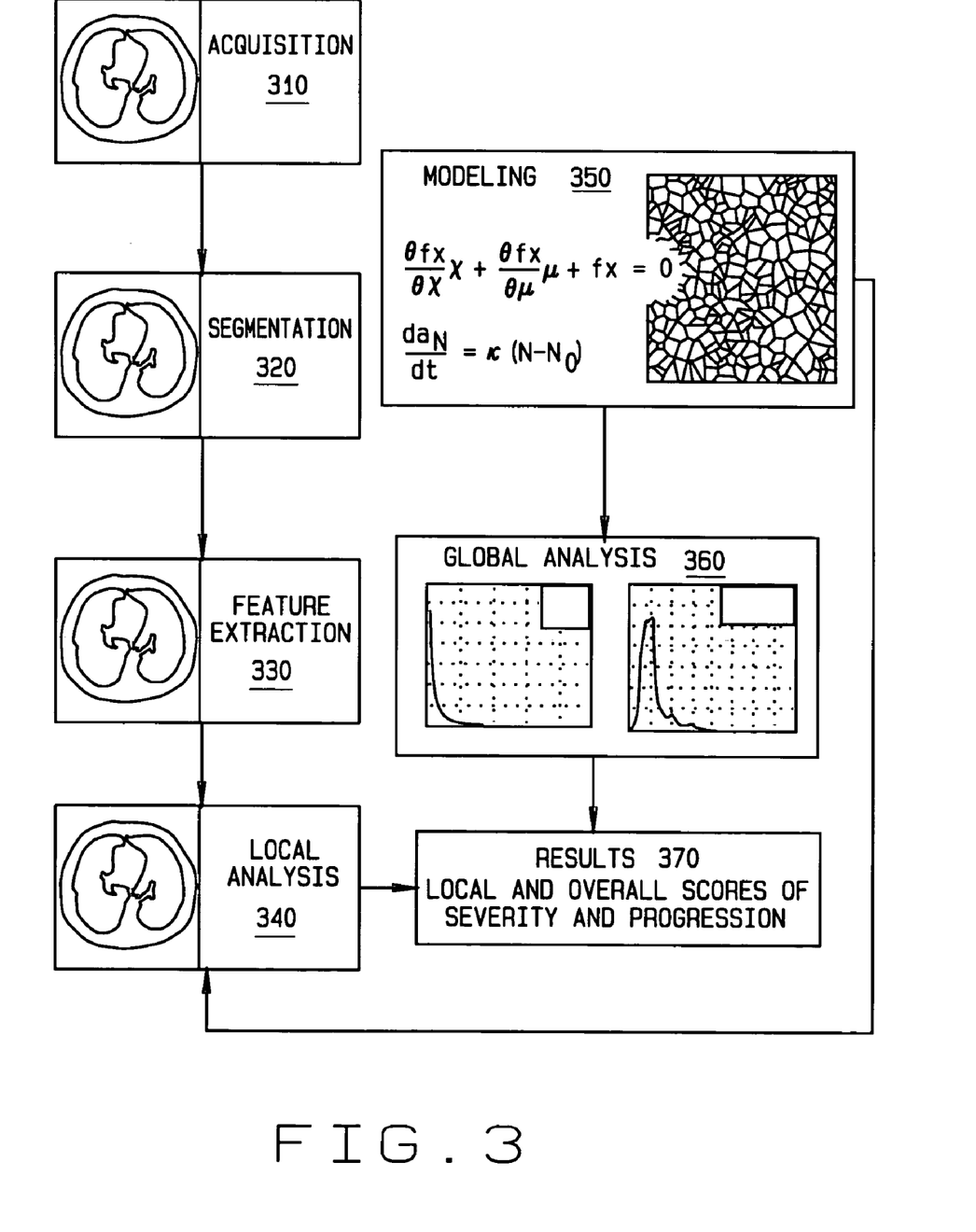
FIG. 3 is a flow chart of a method for measuring, quantifying, and/or predicting disease relevant changes.

In some configurations and referring to FIG. 3, a method for measuring, quantifying and/or predicting disease relevant changes is provided. Thus, a technical effect of configurations represented by FIG. 3 is performed when a user initiates a computer-automated measuring, quantifying, and/or prediction of disease relevant changes. As used herein, the term "disease relevant changes" refers to changes associated with a disease of interest. For example, the number of edges of lung tissue regions, the intensity of affected areas of the lung and the area of the affected areas of the lung are indicators of the presence of emphysema and changes in these aspects indicate progression of the disease. Image data is acquired at 310 and segmented at 320 by a plurality of segmentation steps. The segmentation segments into regions having different properties, for example intensity, area, perimeter, aspect ratio, diameter, variance, derivatives and other properties that may be of interest for a disease. The segmentation steps may be selected from many known segmentation techniques. At 330, feature extraction is performed on the segmented image data to extract relevant features for a disease. These features may include, for example, the number of edges, area and intensity. Acquisition, segmentation, and feature extraction may employ known techniques to extract relevant image information, or, in some configurations, suspicious regions, for a disease. However, in some configurations, further processing is performed at 340 to make predictions relating to certain areas or suspicious regions for use in predicting, quantifying or diagnosing a disease. Thereafter, the areas or suspicious regions can be displayed as an image to the user using one or more techniques known in the art. In some configurations, colored polygons are displayed on top of the image data. The colored polygons or similar highlighted regions correspond to values resulting from the analysis described in greater detail below. The results of the segmented regions are displayed as highlighted regions overlaying the original image data. The display may be two-dimensional (2D) or, in some configurations, three-dimensional (3D).

In some configurations of the present invention, a method for at least one of quantifying, diagnosing and/or predicting disease relevant changes acquired from image data is provided. The method includes applying at least one segmenting process to the image data to generate a plurality of segmented regions of interest and extracting features relevant for a disease from the segmented regions to generate extracted features. The extracted features are modeled for use in at least one of diagnosing, quantifying and/or predicting changes indicative of the given disease. For example, a segmenting step in some configurations comprises segmenting a plurality of sub-regions within a lung and further segmenting for parameters within the sub-regions. The parameters may include edges, area or intensity, or other segmentation parameters, or combinations thereof.

In various configurations and referring further to FIG. 3, a mathematical modeling step 350 enables a biological phenomena to be modeled physically using known physical modeling principles. For example, mathematical modeling is performed using free boundary models such as those that obey von Neumann's Law, which is a known principle used to explain bubble structures or crystal lattice structures made up of a plurality of regions. According to von Neumann's Law, regions with many edges tend to grow and regions with few edges tend to shrink. By modeling anatomical structures and corresponding regions, such as the lung and lung regions, the model detects regions with many edges and few edges. The number of edges is used to predict the possibility of disease progression. Von Neumann's Law holds that regions with 6 edges are stable. An equation for Von Neumann's Law is written:

$$\frac{da_N}{dt} = \kappa(N - N_o)$$ Equation (1)

where N is the number of edges, $N_o$ is 6, and $\kappa$ is a scaling parameter that depends on the physical and chemical properties of the modeled structure. Model biological changes utilizing von Neumann's Law makes it possible to estimate or predict growth or progression of a disease, as regions grow or shrink at a linear rate. Although the effects of emphysema cannot be reversed at this time, the growth or progression of emphysema can be monitored using the principles described above. Thus, behavior of each region can be predicted up to topological changes.

One property of many free boundary models is scale invariance. In models having this property, the normalized distribution $f_x(X/\mu)/\mu$, where X is a random variable associated to a geometric measure of region in the ensemble of regions that form the modeled structure, and $\mu$ is the average value of X, satisfies the differential equation $$\frac{\partial f_x}{\partial x}x + \frac{\partial f_x}{\partial \mu}\mu + f_x = 0.$$ Equation (2)

In models having this property, the comparison of the probability distribution of a geometric parameter, such as area or perimeter, can be compared against a standard provided by the normalized distribution of that same parameter, and deviations or differences in this comparison can be employed as a diagnostic and quantification tool for the disease.

Features relevant for emphysema include the area of affected regions of a lung, the intensity of regions of the lung and the number of edges of regions within the lung. These features can be modeled using von Neumann's Law. Other diseases may also be modeled by von Neumann's Law.

Other known principles and techniques, such as a Potts model, Markov chain, Gibbs chain, Monte Carlo algorithm, diffusion equations, or phase field model, for described regions having a lattice or bubble structure may be used in place of, or in addition to, von Neumann's Law.

Referring further to FIG. 3, modeled regions and extracted features are analyzed in step 340 for local and overall scores of severity and progression. In some configurations, local analysis focuses on a selected region or regions of interest and overall scores focus on disease progression. In many cases, the stage of a disease is determined utilizing factors that may include the areas of disease tissues as compared to areas of healthy tissue, rate of change and spatial distribution of affected areas. As part of diagnosing and treating a patient, scoring is used to stage the patient.

In some configurations of the present invention, extracted features are analyzed to assess severity and progression of a disease. Additionally, in a global analysis step 360 is performed in which the extracted features are processed using at least one histogram analysis.

Some configurations of the present invention further comprise generating output indicative of the level and progression of the disease at 370. For example, the output may be used for staging the disease in a patient, measuring response to therapy, phenotyping for patient selection to participate in drug trials, measuring stability of an anatomical structure and/or prediction of rate of change of the given disease. As used herein, phenotyping refers to observing physical or biochemical characteristics, as determined by both genetic makeup and environmental influences and to express a specific trait, such as stature or blood type, based on the influences. A phenotype is an individual or group of organisms exhibiting a particular phenotype.

Additionally, the output may comprise a display of the analysis results and an identification of suspicious areas extracted using the methods described above. The display may highlight regions in an image corresponding to values from the analysis. In some configurations, colored polygons are displayed on top of the image data. The display may be 2D or 3D.

Some configurations of the present invention provide an apparatus for at least one of quantifying, diagnosing and predicting disease relevant changes utilizing acquired image data. The apparatus comprises an imaging device for acquiring the image data and an image processor. The image processor is configured for applying at least one segmenting process to the image data to generate a plurality of segmented regions of interest and extracting features relevant for a disease from the segmented regions to generate extracted features, and the image processor further configured for mathematically modeling the features for use in one of diagnosing, quantifying and predicting changes indicative of the disease.

Although embodiments of the invention described above locate suspicious regions in CT lung scans, the measuring techniques described above can be directly transferred to other imaging modalities, such as MRI, X-ray, ultrasound, and positron emission tomography (PET). Further, configurations of the invention described above utilize modeling of changes relating to emphysema in the lung, but these techniques can be used to model biological changes in other anatomical regions.

Figure 4:
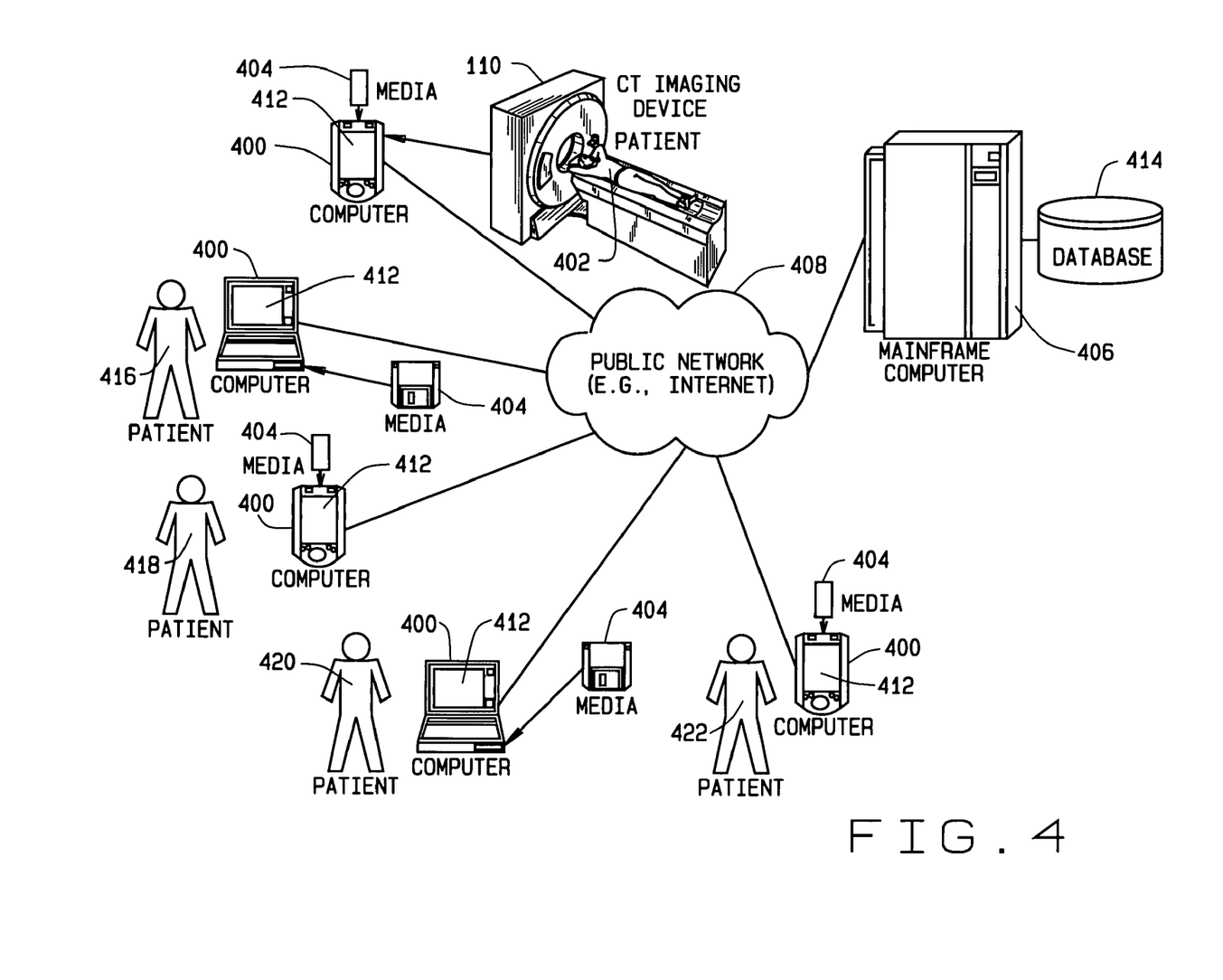
FIG. 4 is a pictorial diagram of a configuration of the present invention for at least one of detecting, quantifying, staging, reporting, and/or tracking of diseases such as chronic obstructive pulmonary disease.

FIG. 4 is representative of a system having a technical effect achieved by a user initiating automated measurements of changeable disease (or other) parameters for patients or objects, and/or facilitating the collection of data from patients for analysis by (for example) a drug company. In some configurations and referring to FIG. 4, a personal computer 400, in the form of a desktop model, a laptop model, a palmtop model, or other suitable form factor is provided to a patient 402 having COPD for management of his or her disease. Software or firmware is also provided, for example, on one or more machine-readable media 404 or from a networked server 406 on a public (or private) network 408 such as the Internet. (Another example of a public or private network that is used in some configurations of the present invention is a hospital network.) So configured, personal computer 400 is thus referred to as a portable, or personal COPD recorder 400. The software or firmware for use in personal COPD recorder 400 is configured to determine metrics for tissue degradation in the patient's lungs and airway inflammation and remodeling, utilizing one or more configurations of the methods and models discussed above with respect to processor 120. For example, the functions of processor 120 and interface unit 130 of FIG. 1 are grouped together in a personal COPD recorder, with the processor of personal computer 400 performing certain of the functions of both processor 120 and interface unit 130. These functions may include those described above for diagnosing, staging, measuring, quantifying, and/or predicting disease relevant changes in patients having emphysema and/or bronchitis, and/or may include similar functions for other disease processes. However, a personal COPD recorder 400 need not necessarily be responsive to activities that may occur in the course of image acquisition. Instead, in many configurations, personal COPD recorder 400 is configured to receive data from an imaging device 110 either through direct connection to imaging device 100 or any other suitable data transfer (such as via machine-readable media and/or via computer network connection). In addition, many configurations of personal COPD recorder 400 are configured to analyze this data at a time selected by patient 402 rather than in real time. It is a design choice as to whether a processor separate from the processor already present in a personal computer used as personal COPD recorder 400 is required in any particular configuration. This choice may be influenced by the speed and computing power provided by the processor in the personal computer.

In some configurations, statistics concerning airway position and size can be used to compare the patient across a population. Use of a free boundary, or foam, model for emphysema enables a comparison of all patients to a common model and the prediction and localization of future changes. Model-based methods also permit incorporation of a priori information. Using techniques such as automated airway segmentation, as discussed above, a scanner model is incorporated directly into the segmentation solution. The tracking framework aids in finding airways in difficult areas. Multiple hypothesis tracking (MHT) capability allows decisions on whether an airway is present in a particular image slice to be delayed until information from neighboring slices is gathered. Additionally, in some configurations, MHT incorporates a predictive model that is used to predict the presence of an airway. Also, MHT is used in some configurations to generate a tree that represents the topology of the airways, and to generate an anatomical atlas. Thus, a complete bronchial tree can be pieced together using multiple hypothesis tracking from cross-sectional imagery.

Results from metrics determined by personal COPD recorder 400 are written into a file format that can be imported into a database 414. This format and capability allows for transmission, integration, and archival of results within a database architecture. In some configurations, the computer or storage system on which database 414 resides may be a networked server 406 from which software programs for personal COPD recorders 400 can be downloaded. In other configurations, database 414 resides on a completely different computer or fileserver. In some configurations, software is made available only in the form of physical media, so no networked server 406 from which software is downloadable to personal COPD recorders 400 is provided. Also in some configurations in which no database 414 is provided, patients such as patient 402 use metrics and monitoring capabilities of their own personal COPD recorder 400 without the aid of analysis obtained from a database of a type represented by database 414. In additional configurations, a database 414 is provided, but not all patients 402, 416, 418, 420, 422, etc. upload data to database 414, and/or not all patients 402, 416, 418, 420, 422, etc. receive the benefits available from the use of database 414.

Portable COPD recorders 400 are provided to a plurality of patients 402, 416, 418, 420, 422, etc. Portable COPD recorder 400 is analogous in some ways to a personal blood glucose monitor, in that a person having COPD recorder 400 can use this device to track his or her own COPD status. In some configurations, personal COPD recorder 400 receives image data from a CT imaging device 110 or other suitable imaging device (e.g., MRI device) at intervals determined by a physician in accordance with the needs of patient 402. Any suitable method may be used to transfer this data, as the transfer need not necessarily occur as patient 402 is scanned. The image data need only be transferred in a manner sufficiently timely to be of use for detecting, quantifying, staging, reporting, and/or tracking a disease. The image data is stored in a memory of COPD recorder 400 and is used to generate the patient's COPD status, which can be displayed on a display screen 412 to patient 402 upon request. In some configurations, personal COPD recorder 400 also provides automated reporting into a database 414 (which may be a distributed database) via a private or public network 408, e.g., the Internet. For example, personal COPD recorder 400 generates and sends a file to a remote database 414 such as a database a pharmaceutical company. Information from recorder 400, together with information gathered from other COPD recorders 400 owned by other patients 416, 418, 420, 422, etc., is reviewed by personnel at pharmaceutical company and used, for example, to evaluate a drug treatment trial and/or to provide personal treatment monitoring. By evaluating each patient's results in accordance with a universal scale, the severity of a disease in any number of patients 402, 416, 418, 420, 422, etc., can be directly compared for diagnosis and triage.

With regular data received from personal COPD recorders 400, a model-based approach for emphysema allows the prediction of rate of growth of the disease. The prediction can by used by a physician to derive a drug treatment schedule and follow-up scan schedule that is advantageous to the patient. COPD recorder 400, by utilizing automated airway segmentation and multiple hypothesis tracking, provides for disease localization, characterization and diagnosis. The model-based approach also allows for the incorporation of other information into the automated diagnostic process, including demographics, diagnosis, and therapy. Predictive models are used in some configurations, such as a foam model for emphysema, which predicts local changes in lung tissue, and incorporation of non-hospital tests, such as stairs and blow. In addition, COPD recorders 400 can operate using a low-dose CT exam, and provide repeatable, robust, trend metrics.

In some configurations of the present invention, one or more computers at a hospital, in a physican's office, or at a physician's workplace is used in the same manner in which the personal computer of a patient is used. In such configurations, the hospital or physician's computer is operated by the physician or a technician or nurse, not necessarily by a patient, who may or may not be present for the analysis of the medical images. In some of these configurations, the hospital or physician computer is on a network, which may be a hospital or other public or private medical network, or the Internet. The automated computer analysis in some configurations is performed for the benefit of the physician or to collect data for drug treatment trials rather than for the direct benefit of the patient.

It will thus be appreciated that various configurations of the present invention allow the diagnosis, stating and/or prediction of COPD from medical images such as computed tomography scans. The automated features provided by the invention via personal computers and software can run with or without the supervision of an experienced physician or scientist, and allow effective disease diagnosis and treatment that can improve a patient's quality of life.

Configurations of the invention are not limited to medical applications, and can be utilized more generally to track changeable parameters of either persons or objects that can be imaged utilizing an imaging device. Tracking can be performed for a plurality of persons or objects, each utilizing a separate associated personal computer for tracking purposes. Results can be aggregated in a remote database and examined in a manner similar to configurations such as those involving drug trials discussed above.

In addition, many of the configurations described herein can also be useful for diagnosing and/or staging, etc., of other diseases, including other diseases that are part of the chronic obstructive pulmonary family, for example and without limitation, asthma. Also, a variety of properties of an image can be analyzed in addition to, or in place of intensity, for example, and without limitation, standard deviation of intensity, region length, and region roundedness.

While the invention has been described in terms of various specific embodiments, those skilled in the art will recognize that the invention can be practiced with modification within the spirit and scope of the claims.

What is claimed is:

1. A method for at least one of detecting, quantifying, staging, reporting, or tracking of a disease, said method comprising:
    providing analysis software configured to at least one of detect, quantify, stage, report, or track a disease of a patient, said analysis software executable on a personal computer of a patient;
    imaging the patient with a medical imaging apparatus;
    downloading medical images of the patient produced by the imaging apparatus to the personal computer of the patient; and
    repeating said imaging and downloading a plurality of times at intervals selected to provide said analysis software with sufficient images to at least one of detect, quantify, stage, report, or track the disease in the patient by computer analysis of the images via the analysis software executable on the personal computer of the patient.

2. A method in accordance with claim 1 wherein said imaging apparatus is a computed tomographic imaging apparatus.

3. A method in accordance with claim 1 wherein said imaging apparatus is a magnetic resonance imaging apparatus.

4. A method in accordance with claim 1 wherein said imaging apparatus is an x-ray imaging apparatus.

5. A method in accordance with claim 1 wherein the disease is chronic obstructive pulmonary disease, and said analysis software is configured to analyze tubular structures depicted in the medical images.

6. A method in accordance with claim 5 wherein the disease is selected from the group consisting of chronic bronchitis and asthma.

7. A method in accordance with claim 5 wherein said analysis software is configured to analyze bronchial wall cross-sectional area in the medical images.

8. A method in accordance with claim 5 wherein said analysis software is configured to utilize segmentation to isolate a selected tubular structure of interest in the medical images.

9. A method in accordance with claim 8 wherein said analysis software is configured to measure bronchial wall cross-sectional area utilizing said isolated selected tubular structure of interest.

10. A method in accordance with claim 5 wherein said analysis software is further configured to identify a center of an airway lumen in the medical images.

11. A method in accordance with claim 10 wherein said analysis software is configured to measure bronchial wall cross-sectional area utilizing said identified center of an airway lumen in the medical images.

12. A method in accordance with claim 1 wherein the disease is chronic obstructive pulmonary disease, and said analysis software is configured to analyze areas of a lung infected with the disease in the medical images.

13. A method in accordance with claim 12 wherein the disease is emphysema.

14. A method in accordance with claim 12 wherein said analysis software is configured to divide an image of a lung into a series of regions to be analyzed.

15. A method in accordance with claim 1 wherein the disease is chronic obstructive pulmonary disease, and said analysis software is configured to analyze properties of regions of a lung in the medical images.

16. A method in accordance with claim 1 wherein the disease is chronic obstructive pulmonary disease and said analysis software is configured to analyze region edges in a lung in the medical images.

17. A method in accordance with claim 1 wherein said analysis software is configured to analyze airway segmentation and perform multiple hypothesis tracking.

18. A method in accordance with claim 17 wherein said analysis software is configured to analyze a bronchial tree and to use multiple hypothesis tracking to piece a bronchial tree together from cross-sectional images.

19. A network for at least one of detecting, quantifying, staging, reporting, or tracking of a disease, said network comprising:
    analysis software executable on personal computers of patients, said software including instructions configured to instruct the personal computer to at least one of detect, quantify, stage, report, or track a disease by computer analysis of images of a patient; and
    an interface for transferring scanned images of a patient to a personal computer of the imaged patient.

20. A network in accordance with claim 19 further comprising a remote database, and wherein said analysis software is configured to instruct a personal computer to transmit information relating to status of a patient's disease to said remote database.

21. A network in accordance with claim 20 wherein said database is maintained by a pharmaceutical company.

22. A network in accordance with claim 20 wherein said analysis software is configured to transmit information relating to the status of a patient's disease in accordance with a universal scale.

23. A network in accordance with claim 19 wherein said scanned images are produced by a computed tomographic imaging apparatus.

24. A network in accordance with claim 19 wherein said scanned images are produced by a magnetic resonance imaging apparatus.

25. A network in accordance with claim 19 wherein said scanned images are produced by an x-ray imaging apparatus.

26. A network in accordance with claim 19 wherein the disease is chronic obstructive pulmonary disease, and said analysis software is configured to analyze tubular structures depicted in the medical images.

27. A network in accordance with claim 26 wherein the disease is selected from the group consisting of chronic bronchitis and asthma.

28. A network in accordance with claim 26 wherein said analysis software is configured to analyze bronchial wall cross-sectional area in the medical images.

29. A network in accordance with claim 26 wherein said analysis software is configured to utilize segmentation to isolate a selected tubular structure of interest in the medical images.

30. A network in accordance with claim 29 wherein said analysis software is configured to measure bronchial wall cross-sectional area utilizing said isolated selected tubular structure of interest.

31. A network in accordance with claim 26 wherein said analysis software is further configured to identify a center of an airway lumen in the medical images.

32. A network in accordance with claim 31 wherein said analysis software is configured to measure bronchial wall cross-sectional area utilizing said identified center of an airway lumen in the medical images.

33. A network in accordance with claim 19 wherein the disease is chronic obstructive pulmonary disease, and said analysis software is configured to analyze areas of a lung infected with the disease in the medical images.

34. A network in accordance with claim 33 wherein the disease is emphysema.

35. A network in accordance with claim 33 wherein said analysis software is configured to divide an image of a lung into a series of regions to be analyzed.

36. A network in accordance with claim 19 wherein the disease is chronic obstructive pulmonary disease, and said analysis software is configured to analyze properties of regions of a lung in the medical images.

37. A network in accordance with claim 19 wherein the disease is chronic obstructive pulmonary disease and said analysis software is configured to analyze region edges in a lung in the medical images.

38. A network in accordance with claim 19 wherein said analysis software is configured to analyze airway segmentation and perform multiple hypothesis tracking.

39. A network in accordance with claim 38 wherein said analysis software is configured to analyze a bronchial tree and to use multiple hypothesis tracking to piece a bronchial tree together from cross-sectional images.

40. A computing device configured to:
download medical images of a patient produced by an imaging apparatus to a computing device of a patient;
analyze said downloaded medical images to at least one of detect, quantify, stage, report, or track a disease in the patient and report analysis results to the patient via an image analysis software executable on the computing device of the patient; and
transmit results of said analysis to a remote database.

41. A computing device in accordance with claim 40, wherein to transmit results of said analysis to a remote database, said computing device is configured to transmit information relating to the status of a patient's disease in accordance with a universal scale.

42. A computing device in accordance with claim 40 configured to download said medical images from a computed tomographic imaging apparatus.

43. A computing device in accordance with claim 40 configured to download said medical images from a magnetic resonance imaging apparatus.

44. A computing device in accordance with claim 40 configured to download said medical images from an x-ray imaging apparatus.

45. A computing device in accordance with claim 40 wherein the disease is chronic obstructive pulmonary disease, and said computing device is configured to analyze tubular structures depicted in the medical images.

46. A computing device in accordance with claim 45 configured to analyze bronchial wall cross-sectional area in the medical images.

47. A computing device in accordance with claim 45 configured to utilize segmentation to isolate a selected tubular structure of interest in the medical images.

48. A computing device in accordance with claim 45 further configured to identify a center of an airway lumen in the medical images.

49. A computing device in accordance with claim 40 wherein the disease is chronic obstructive pulmonary disease, and said computing device is configured to analyze regions of a lung infected with the disease in the medical images.

50. A computing device in accordance with claim 40 wherein the disease is chronic obstructive pulmonary disease, and said computing device is configured to analyze intensity of regions of a lung in the medical images.

51. A computing device in accordance with claim 40 wherein the disease is chronic obstructive pulmonary disease and said computing device is configured to analyze region edges in a lung in the medical images.

52. A computing device in accordance with claim 40 configured to analyze airway segmentation and perform multiple hypothesis tracking.

53. A method for performing a drug treatment trial comprising:
providing analysis software configured to at least one of detect, quantify, stage, report, or track a disease of a patient, said analysis software executable on personal computers of a plurality of patients;
imaging the patients with medical imaging apparatus to produce medical images of the patients;
downloading the medical images of each imaged patient to the personal computer of the imaged patient;
repeating said imaging and downloading a plurality of times at intervals selected to provide said analysis software with sufficient images to at least one of detect, quantify, stage, report, or track the disease in each patient;
analyzing said medical images utilizing the personal computers of each patient to at least one of detect, quantify, stage, report, or track a disease in the patient by computer analysis of the images via the analysis software executable on the personal computer of the patient; and
uploading results of the analysis from each patient's personal computer to a database for further analysis and evaluation.

54. A method for tracking a changeable parameter of a person, said method comprising:
imaging the person with an imaging apparatus;
downloading images of the person produced by the imaging apparatus to a personal computer of the person; and
repeating said imaging and downloading a plurality of times at intervals selected to provide an analysis software with sufficient images to track said at least one changeable parameter by computer analysis of the images via the analysis software executable on the personal computer of the patient.

55. A method in accordance with claim 54 carried out on a plurality of persons, utilizing a separate personal computer for each person or object.

56. A method in accordance with claim 55 further comprising aggregating said changeable physical parameters in a remote database.

57. A method for at least one of detecting, quantifying, staging, reporting, or tracking of a disease, said method comprising:
   imaging a patient with a medical imaging apparatus;
   downloading medical images of the patient produced by the imaging apparatus to a personal computer of the patient; and
   repeating said imaging and downloading a plurality of times at intervals selected to provide an analysis software with sufficient images to at least one of detect, quantify, stage, report, or track the disease in the patient by computer analysis of the images via the analysis software executable on the personal computer of the patient.

58. A method in accordance with claim 57 wherein said computer on a network is a computer at a hospital or in a physician's office or workplace.

59. A method in accordance with claim 57 wherein said imaging apparatus is a computed tomographic imaging apparatus.

60. A method in accordance with claim 57 wherein said imaging apparatus is a magnetic resonance imaging apparatus.

61. A method in accordance with claim 57 wherein said imaging apparatus is an x-ray imaging apparatus.

62. A method in accordance with claim 57 wherein the disease is chronic obstructive pulmonary disease, and said analysis software is configured to analyze tubular structures depicted in the medical images.

63. A method in accordance with claim 62 wherein the disease is selected from the group consisting of chronic bronchitis and asthma.

64. A method in accordance with claim 62 wherein said analysis software is configured to analyze bronchial wall cross-sectional area in the medical images.

65. A method in accordance with claim 62 wherein said analysis software is configured to utilize segmentation to isolate a selected tubular structure of interest in the medical images.

66. A method in accordance with claim 65 wherein said analysis software is configured to measure bronchial wall cross-sectional area utilizing said isolated selected tubular structure of interest.

67. A method in accordance with claim 62 wherein said analysis software is further configured to identify a center of an airway lumen in the medical images.

68. A method in accordance with claim 67 wherein said analysis software is configured to measure bronchial wall cross-sectional area utilizing said identified center of an airway lumen in the medical images.

69. A method in accordance with claim 57 wherein the disease is chronic obstructive pulmonary disease, and said analysis software is configured to analyze areas of a lung infected with the disease in the medical images.

70. A method in accordance with claim 69 wherein the disease is emphysema.

71. A method in accordance with claim 69 wherein said analysis software is configured to divide an image of a lung into a series of regions to be analyzed.

72. A method in accordance with claim 57 wherein the disease is chronic obstructive pulmonary disease, and said analysis software is configured to analyze properties of regions of a lung in the medical images.

73. A method in accordance with claim 57 wherein the disease is chronic obstructive pulmonary disease and said analysis software is configured to analyze region edges in a lung in the medical images.

74. A method in accordance with claim 57 wherein said analysis software is configured to analyze airway segmentation and perform multiple hypothesis tracking.

75. A method in accordance with claim 74 wherein said analysis software is configured to analyze a bronchial tree and to use multiple hypothesis tracking to piece a bronchial tree together from cross-sectional images.

* * * * *